(12) United States Patent
Nakamura et al.

(10) Patent No.: US 9,131,920 B2
(45) Date of Patent: Sep. 15, 2015

(54) ULTRASONIC PROBE AND ULTRASONIC IMAGE DIAGNOSTIC DEVICE

(75) Inventors: Tomoaki Nakamura, Nagano (JP); Hiroaki Hosomi, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 101 days.

(21) Appl. No.: 13/606,132

(22) Filed: Sep. 7, 2012

(65) Prior Publication Data

US 2013/0072796 A1    Mar. 21, 2013

(30) Foreign Application Priority Data

Sep. 20, 2011    (JP) .................................. 2011-204300

(51) Int. Cl.
A61B 8/13    (2006.01)
A61B 8/00    (2006.01)
A61B 8/08    (2006.01)

(52) U.S. Cl.
CPC .............. A61B 8/4272 (2013.01); A61B 8/4427 (2013.01); A61B 8/4455 (2013.01); A61B 8/08 (2013.01)

(58) Field of Classification Search
None
See application file for complete search history.

(56) References Cited

U.S. PATENT DOCUMENTS

| 4,545,385 A * | 10/1985 | Pirschel ........................ 600/445 |
| 5,197,475 A * | 3/1993 | Antich et al. .................. 600/437 |
| 8,062,225 B1 * | 11/2011 | Prager et al. .................. 600/459 |
| 8,110,963 B2 | 2/2012 | Funasaka et al. |
| 8,169,855 B2 | 5/2012 | Nakamura |
| 2007/0032726 A1 * | 2/2007 | Osaka et al. ................... 600/459 |
| 2008/0161693 A1 * | 7/2008 | Prager et al. ................... 600/459 |
| 2011/0115337 A1 | 5/2011 | Nakamura et al. |
| 2011/0194380 A1 * | 8/2011 | Fukutani ....................... 367/140 |
| 2011/0227449 A1 * | 9/2011 | Nakamura ..................... 310/317 |
| 2012/0099404 A1 | 4/2012 | Funasaka et al. |

FOREIGN PATENT DOCUMENTS

| JP | 2006-198162 A | 8/2006 |
| JP | 2006-212287 A | 8/2006 |
| JP | 2009-025179 A | 2/2009 |
| JP | 2009-036623 A | 2/2009 |
| JP | 2010-165341 A | 7/2010 |
| JP | 2010-183437 A | 8/2010 |
| JP | 2010-210283 A | 9/2010 |
| JP | 2011-124973 A | 6/2011 |
| JP | 2011-217351 A | 10/2011 |

* cited by examiner

*Primary Examiner* — Sanjay Cattungal
*Assistant Examiner* — Kevin Pontius
(74) *Attorney, Agent, or Firm* — Global IP Counselors, LLP

(57) ABSTRACT

An ultrasonic probe includes a substrate having an opening section, a support film disposed on the substrate, a piezoelectric body disposed on the support film at the opening section, first and second resin sections, and a communicating section. The first resin section is disposed at a position overlapping the opening section in the plan view and spaced apart from the support film with the liquid being arranged therebetween. The communicating section is connected to the first resin section. The second resin section is connected to the communicating section to house the liquid flowing in through a communication hole of the communicating section. At least portions of the first and second resin sections are configured to deform such that a first liquid filled volume formed between the first resin section and the support film and a second liquid filled volume formed by the second resin section are changed.

2 Claims, 9 Drawing Sheets

ULTRASONIC PROBE AND ULTRASONIC IMAGE DIAGNOSTIC DEVICE

CROSS-REFERENCE TO RELATED APPLICATIONS

This application claims priority to Japanese Patent Application No. 2011-204300 filed on Sep. 20, 2011. The entire disclosure of Japanese Patent Application No. 2011-204300 is hereby incorporated herein by reference.

BACKGROUND

1. Technical Field

The present invention relates to an ultrasonic probe that transmits an ultrasonic wave to a test object and receives a reflected wave (echo) from the test object and also relates to an ultrasonic image diagnostic device that uses the ultrasonic probe.

2. Related Art

There is a known conventional ultrasonic sensor that detects a position or state of a test object using an ultrasonic transducer configured to emit and receive ultrasonic waves (see Japanese Laid-Open Patent Publication No. 2009-25179).

Japanese Laid-Open Patent Publication No. 2009-25179 discloses an liquid detecting unit (ultrasonic sensor) comprising an ultrasonic wave output section equipped with an ultrasonic transducer and an acoustic impedance matching layer provided on the ultrasonic wave output section. This liquid detecting unit has an ultrasonic wave receiving/emitting surface formed on a portion of one side of the ultrasonic wave output section. The acoustic impedance matching layer is formed on the one side of the ultrasonic wave output section, and an output surface that outputs ultrasonic waves is provided on the opposite side of the acoustic impedance matching layer as the ultrasonic wave output section. A fluid binder holding recess is formed in the output surface and when the output surface of the liquid detecting unit is to be put into contact with a container, the fluid binder holding recess is filled with a fluid binder before the output surface is made to contact the container. Also disclosed is a configuration in which a cylindrical recess forming member is provided in the one side of the ultrasonic wave output section and a fluid binder holding recess is formed by filling an interior of the recess forming member with ah acoustic impedance layer. When the output surface is to be touched against a container, the fluid binder holding recess is filled with a fluid binder.

SUMMARY

When a state of a living organism is to be detected using an ultrasonic transducer, it is feasible to touch the output surface of the liquid detecting unit disclosed in the above mentioned publication against the organism and execute transmission and reception of ultrasonic waves. In order to detect the state of the organism in a favorable manner, it is preferable for the output surface to make intimate contact with the organism.

However, with the technology presented in the above mentioned publication, the fluid binder holding recess is formed in the output surface and the fluid binder holding recess is filled with a fluid binder when the output surface is touched against the organism. If the fluid binder flows out of the fluid binder holding recess, then there is a possibility that intimate contact between the organism and the output surface cannot be achieved and bubbles will develop between the organism and the output surface. When this occurs, ultrasonic waves will be reflected by the bubbles and the ability to accomplish a proper detection will be compromised. In view of this problem, it is feasible to omit providing a recess and make the output surface flat so that the output surface can be pressed against the organism with intimate contact. However, in such a case, although intimate contact is achieved between the organism and the output surface, when the output surface deflects inward, the ultrasonic wave receiving/emitting surface of the ultrasonic transducer provided adjacent to the acoustic impedance layer also undergoes deformation.

It is also feasible to adopt a configuration in which the cylindrical recess forming member is formed on the one side of the ultrasonic wave output section where the ultrasonic wave receiving/emitting surface is provided, the output surface is formed on an end portion of the recess forming member, the interior of the recess forming member is sealed closed, and a liquid acoustic impedance layer is provided inside the sealed recess forming member. However, with this configuration, too, when the output surface is put into intimate contact with a living organism, the internal pressure of the liquid acoustic impedance layer increases due to deflection of the output surface and this internal pressure also causes the ultrasonic wave receiving/emitting surface to undergo deformation.

When the ultrasonic transducer deforms in this way, the displacement amount of the vibrations of the ultrasonic wave receiving/emitting surface decreases and ultrasonic waves cannot be received and emitted as favorably.

The object of the present invention is to provide an ultrasonic probe and an ultrasonic wave image diagnostic device that can receive and emit ultrasonic waves in a favorable manner.

An ultrasonic probe according to one aspect of the present invention includes a substrate, a support film, a piezoelectric body, a first resin section, a liquid, a communicating section, and a second resin section. The substrate has an opening section. The support film is disposed on the substrate and covers one side of the opening section. The piezoelectric body is disposed on the support film at a position inside of the opening section when viewed in a plan view along a thickness direction of the support film. The first resin section is disposed at a position overlapping the opening section in the plan view and spaced apart from the support film in the thickness direction of the support film. The liquid is arranged between the first resin section and the support film. The communicating section is connected to the first resin section and having a communication hole through which the liquid can flow. The second resin section is connected to the communicating section and configured to house the liquid that flows in through the communication hole. At least a portion of the first resin section and at least a portion of the second resin section are configured to deform such that a first liquid filled volume formed between the first resin section and the support film and a second liquid filled volume formed by the second resin section are changed.

With this aspect of the present invention, when the first resin section is pressed against a human body or other test object, the first resin section deforms and liquid inside the first space flows into the second space. Thus, even if the ultrasonic probe is moved during testing, the first resin section constantly maintains excellent contact with the test object.

The test object is in intimate contact with the first resin section and even if the internal pressure of the first space increases, deformation of the support film can be suppressed. Consequently, when a voltage is applied to the piezoelectric body and the support film is made to vibrate or when an ultrasonic wave is received by the support film such that the support film vibrates, the vibration of the support film is not attenuated and the support film can emit or receive the ultrasonic wave in a favorable manner.

The ultrasonic probe according to the above described aspect of the present invention is preferably configured such that a plurality of the opening sections having the same surface area are provided at constant intervals and the piezoelectric material is arranged inside each of the opening sections in the plan view.

With this aspect of the present invention, since ultrasonic waves can be transmitted and received by vibration of the support film covering the opening sections, a high-resolution echo image can be acquired by receiving reflected ultrasonic waves (echo) utilizing the opening sections having the same surface area and provided at constant intervals.

In the ultrasonic probe according to the above described aspect of the present invention, the opening sections of the substrate preferably pass through the substrate in a thickness direction of the substrate, the support film preferably covers one side of the substrate, the first resin section preferably has a first recessed section that opens toward the support film and forms the first liquid filled volume by an opening edge of the first recessed section being connected to the other side of the substrate that is opposite from the one side, and the second resin section preferably has a second recessed section that opens toward the support film and forms the second liquid filled volume by an opening edge of the second recessed section being connected to the other side of the substrate.

In a configuration in which the opening ends of the recessed sections are connected to the support film covering the one side of the substrate, when the first resin section facing the opening section of the substrate is pressed strongly against a test object, there is a possibility that the touching section of the first resin section will contact the support film and contact the piezoelectric material provided on the support film. This could damage the support film and the piezoelectric material.

Conversely, with this aspect of the present invention, the opening end of the first recessed section of the first resin section and the opening end of the second recessed section of the second resin section are connected to the other side of the substrate which is not covered by the support film. Consequently, the first space includes the interior of the first recessed section and a region inside the opening section. Thus, when the first resin section is pressed strongly against a test object and the touching section deflects greatly toward the support film, the pressed portion contacts the substrate. That is, the touching section does not contact the support film or the piezoelectric material and damage to the support film and the piezoelectric material can be prevented.

The ultrasonic probe according to the above described aspect of the present invention preferably includes a displacement detecting section configured to detect a displacement of the second resin section, and an ultrasonic wave receiving/emitting section configured to apply a voltage to the piezoelectric bodies when the displacement detecting section detects a displacement of the second resin section.

With this aspect of the present invention, a displacement detecting means is provided to detect a displacement of the second resin section. Thus, contact of the test object against the touching section can be detected by the displacement detecting means detecting a displacement of the second resin section. As a result, by executing emission and reception of ultrasonic waves with the ultrasonic way receiving/emitting means after the displacement detecting means has detected that the touching section has touched the test object, the ultrasonic waves can be ensured to reach the test object.

An ultrasonic probe according to another aspect of the present invention includes a case, a liquid filled section, a contact section, a flexible section and an ultrasonic transducer. The liquid filled section is filled with a liquid. The contact section includes a deformable resin material, is positioned outside the case, and forms a portion of the liquid filled section. The flexible section includes a deformable resin material and forms a portion of the liquid filled section. The ultrasonic transducer is positioned between the contact section and the case. The ultrasonic probe is configured to transmit ultrasonic waves to a test object through the contact section.

With this configuration, since the liquid filled space is formed by a pliable contact section and a pliable flexible section, the flexible section deforms when the contact section is pressed against a test object such that the contact section deforms.

In this ultrasonic probe according to the above aspect of the present invention, it is acceptable for the flexible section to be positioned outside the case. With such a configuration, it is possible to visually recognize deformation of the flexible section in response to deformation of the contact section.

In this ultrasonic probe according to the above aspect of the present invention, it is acceptable for the flexible section to be positioned inside the case. With such a configuration, the flexible section will not be touched by accident during work and, thus, the intimate contact between the touching section and the test object will not be disrupted.

An ultrasonic image diagnostic device according to another aspect of the present invention includes the ultrasonic probe explained heretofore. As explained previously, with these aspects of the invention a better quality of intimate contact can be achieved between the test object and the touching section and a high-resolution echo image can be acquired.

BRIEF DESCRIPTION OF THE DRAWINGS

Referring now to the attached drawings which form a part of this original disclosure:

FIGS. 2A and 2B show main parts of an ultrasonic probe used in an ultrasonic image diagnostic device according to the first embodiment, wherein FIG. 2A shows one example and FIG. 2B shows a variation of FIG. 2A.

DETAILED DESCRIPTION OF EXEMPLARY EMBODIMENTS

First Embodiment

A first embodiment of the present invention will now be explained.

Figure 1:
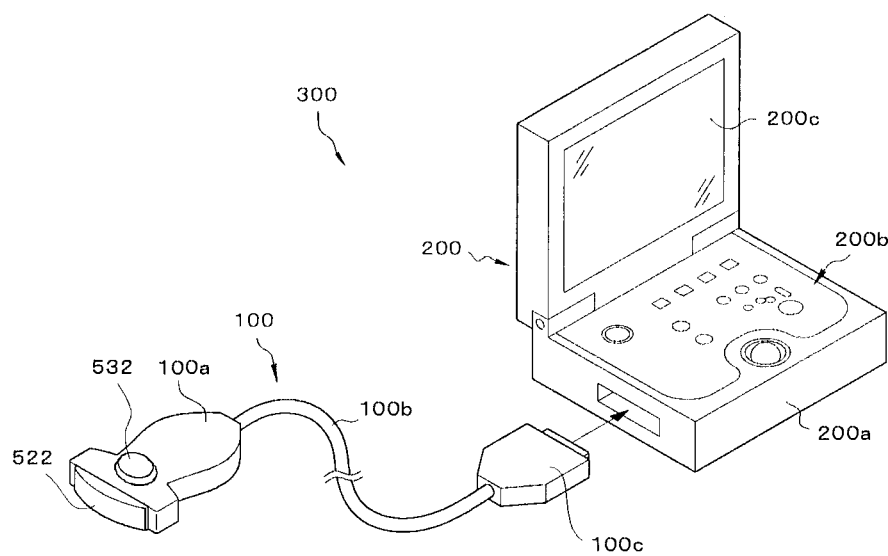
FIG. 1 is a schematic view of an ultrasonic image diagnostic device according to a first embodiment of the present invention.

FIG. 1 is a schematic view showing constituent features of an ultrasonic image diagnostic device 300, and FIG. 2 shows main parts of an ultrasonic probe 100 used in the ultrasonic image diagnostic device 300. FIG. 3 is a simplified sectional view showing an ultrasonic wave receiving/emitting section 10 of a test device 1 provided inside the ultrasonic probe 100.

Ultrasonic Image Diagnostic Device

As shown in FIG. 1, the ultrasonic image diagnostic device 300 according to this embodiment comprises an ultrasonic probe 100 and an ultrasonic wave observing device 200. The ultrasonic wave probe 100 comprises a case 100a, a cable 100b, and a connector 100c. The case 100a has a contact section 522 serving as a portion that contacts a test object and a flexible section 532. The contact section 522 and the flexible section 532 are exposed on the exterior of the case 100a.

The ultrasonic wave observing device 200 has a device main body 200a to which the ultrasonic probe 100 is connected, an operating section 200b that an operator uses to set drive conditions of the ultrasonic probe 100, and a display monitor 200c on which an echo image of a test object is displayed.

Figure 2A:
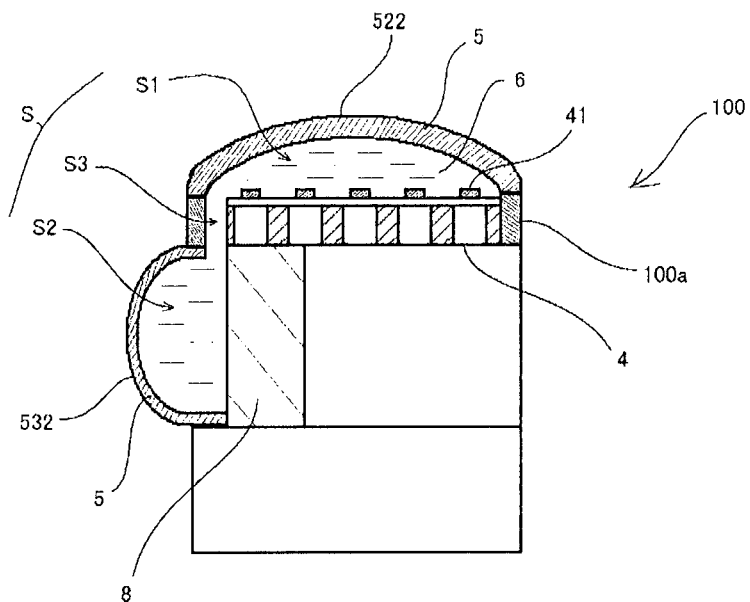
Figure 3:
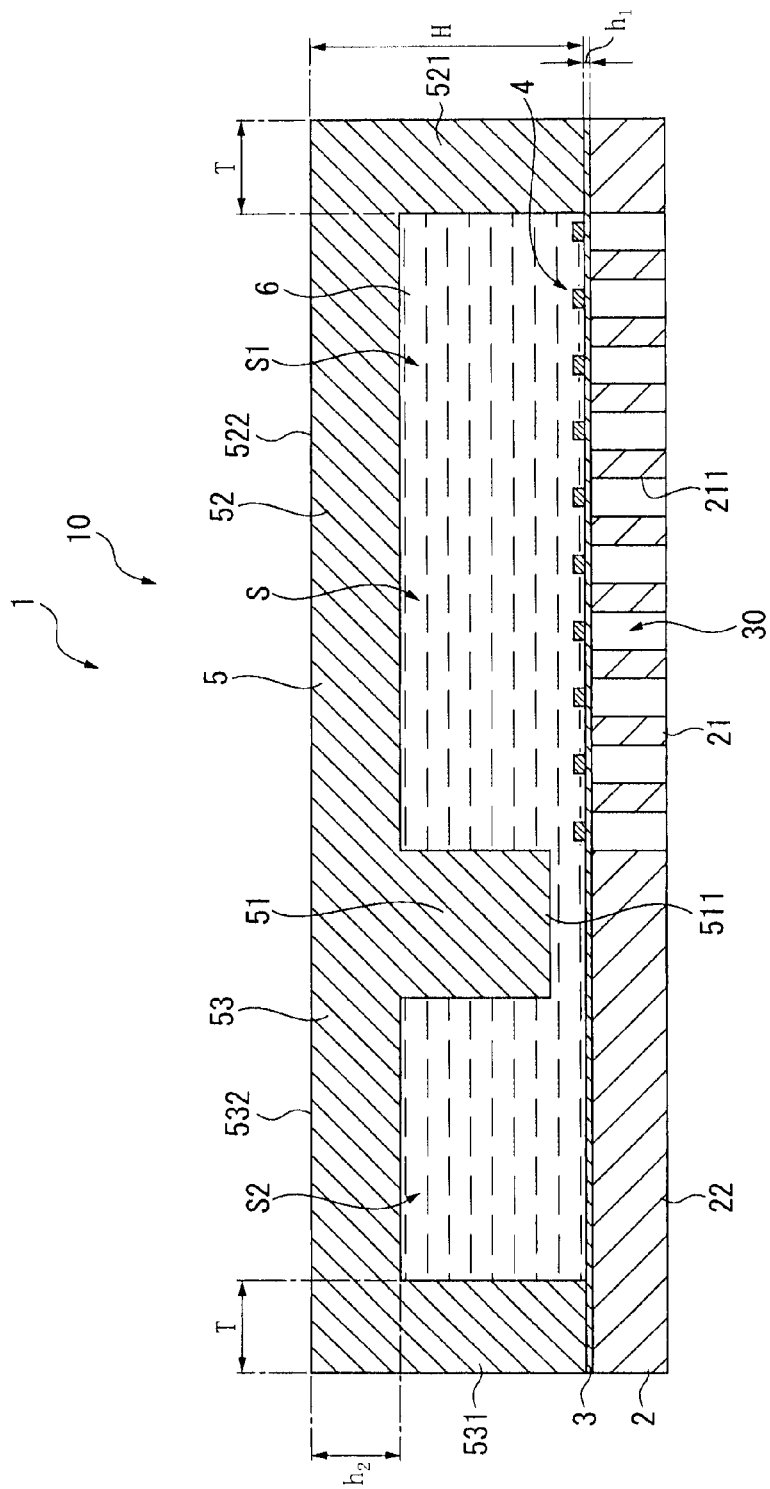
FIG. 3 is a simplified sectional view showing main parts of an ultrasonic probe according to the first embodiment.

FIG. 2A shows a configuration of the main parts of the ultrasonic probe 100 used in the ultrasonic image diagnostic device. The contact section 522 for contacting a test object is made of a pliable resin material 5. Similarly to the contact section 522, the flexible section 532 is also made of the resin material 5. An ultrasonic transducer having a plurality of piezoelectric bodies 41 arranged in an array form is provided. The ultrasonic transducer 4 and the resin material 5 surround a space S, and the space S is divided into a space S1 and a space S2 that communicate with each other through a space S3. The space S is filled with a liquid ultrasonic wave transmitting medium 6. That is, the space S is a liquid filled space.

When the contact section 522 is pressed against the test object, the contact section 522 deforms so as to conform to the contours of the test object and enable the contact section 522 to achieve intimate contact with the test object, thereby enabling ultrasonic waves to be transmitted between the test object and the ultrasonic transducer 4.

The ultrasonic wave transducer 4 is connected to a control section 8 that controls and drives the piezoelectric bodies 41. The ultrasonic probe 100 according to the present invention includes at least the contact section 522, the flexible section 532, the space S, the ultrasonic wave transmitting medium 6, the ultrasonic transducer 4, and the controls section 8. In this embodiment, the contact section 522 and the flexible section 532 are made of the same resin material 5, but it is acceptable to use different materials so long as both are pliable materials.

Although in the example shown in FIG. 2A the contact section 522 and the flexible section 532 are both exposed on the exterior of the case 100a, it is acceptable to adopt a structure in which the flexible section 532 is not exposed to the outside. In the ultrasonic receiving/emitting section 10 according to the present invention, the flexible section 532 deforms in an expanding manner when the contact section 522 is pressed and deforms. Therefore, it is preferable to use the probe in a way that avoids allowing the flexible section 532 to contact an outside object.

Figure 2B:
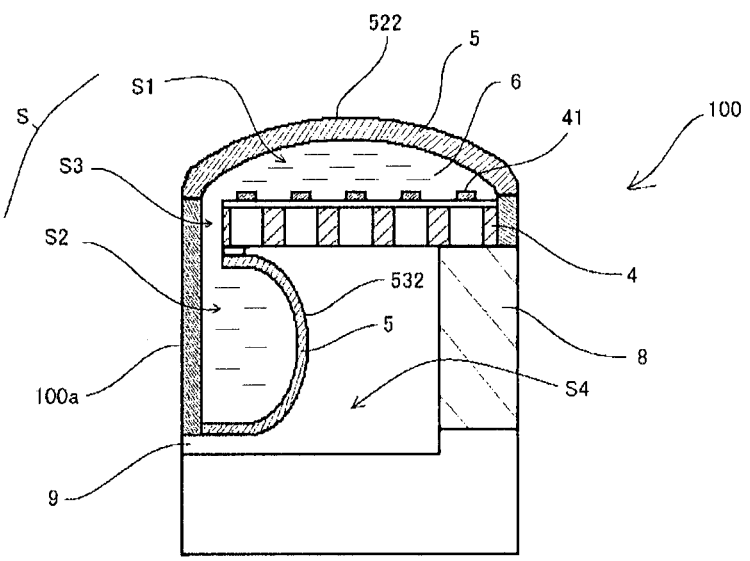

FIG. 2B shows a variation of the example shown in FIG. 2A. In this variation, the flexible section 532 is provided inside the case 100a such that the flexible section 532 cannot be touched from outside the case 100a. A fourth space S4 in which the flexible section 532 is arranged communicates with the outside through an air hole 9. With this configuration, it is possible to prevent a situation in which the flexible section 532 is pressed while a user is working with the device and it becomes difficult for the contact section 522 to deform, resulting in poor contact with respect to the test object.

Ultrasonic Wave Receiving/Emitting Section

As shown in FIG. 3, the ultrasonic wave receiving/emitting section 10 of the test device 1 is basically comprises a sensor array substrate 2 serving as a substrate, a support film 3 laminated onto the sensor array substrate 2, a plurality of ultrasonic transducers 4 configured to receive and emit ultrasonic waves, a resin material 5 that covers the support film 3 and forms a space S between itself and the support film 3, and a liquid ultrasonic wave transmitting medium 6 that fills the space S. The constituent features of the ultrasonic transducers 4 will now be explained.

The sensor array substrate 2 comprises a first support section 21 that is a region in which the ultrasonic transducers 4 are arranged and a second support section 22 that is adjacent to an outer periphery of the first support section 21. The sensor array substrate 2 is made of, for example, crystalline silicon (Si) or another semiconductor material. Opening sections 211 that are substantially circular in a plan view (sensor plan view), i.e., when the sensor array substrate 2 is viewed from a direction perpendicular to a substrate surface of the sensor array substrate 2, are formed in the sensor array substrate 2 in positions corresponding to the positions of the ultrasonic transducers 4. The radius a of the opening sections 211 is, for example, approximately 50 μm.

The support film 3 is formed on the sensor array substrate 2 with a uniform thickness dimension. As a result, the opening sections 211 are blocked by the support film 3. The thickness dimension h1 of the support film 3 is, for example, 2 μm. In the explanation that follows, the portions of the support film 3 that block the opening sections 211 are called diaphragms 30.

More specifically, the support film 3 has a two-layer structure comprising an $SiO_2$ layer formed on the sensor array substrate 2 and a $ZrO_2$ layer formed on the $SiO_2$ layer. The support film 3 is made by, for example, first forming the $SiO_2$ layer by thermally oxidizing the sensor array substrate 2, which is made of silicon (Si). Then, a Zr layer is deposited onto the $SiO_2$ layer and the Zr layer is thermally oxidized to form the $ZrO_2$ layer.

In addition to giving the support film 3 a two-layer structure comprising an $SiO_2$ layer and a $ZrO_2$ layer, in this embodiment the two layers of the support film 3 are configured such that the Young's modulus E of the support film 3 is approximately 70 GPa in accordance with the calculation explained below. Since the radius a of the opening sections 211 is 50 μm as mentioned previously, the radius a of the diaphragms 30 is also 50 μm and, therefore, the surface area of the same is $7.85 \times 10^{-3}$ $mm^2$. The flexural rigidity D of the diaphragms 30 is $5.13 \times 10-8$ (Pa-m3) when calculated according to the equation (1) shown below and assuming the Poisson's ratio ν is 0.3.

With this embodiment, the opening sections 211 are circular to achieve a good balance of stress when the diaphragms 30 deflect. However, it is acceptable for the opening sections 211 to be another shape, e.g., rectangular or elliptical.

Equation (1)

$$D = \frac{Eh^3}{12(1-\nu^2)} \quad (1)$$

D: flexural rigidity (Pa·m³), E: Young's modulus (Pa), h: thickness dimension (m), ν: Poisson's ratio Based on the flexural rigidity D, the maximum deflection amount $\omega_{max}$ of the diaphragms 30 blocking the opening sections 211 is $1.9 \times 10^{-12} \times q$ (m) when calculated according to the equation (2) shown below.

Equation (2)

$$\omega_{max} = \frac{qa^4}{64D} \quad (2)$$

$\omega_{max}$: maximum deflection amount (m), q: load per unit area (Pa), a: radius of opening sections and diaphragms (m)

The resin material 5 is in intimate contact with an outer periphery of the support film 3 on the sensor array substrate 2 and configured to surround the sensor array substrate 2 such that a space S is formed between the resin material 5 and the sensor array substrate 2. The space S is sealed from the external space outside the device. The space S is filled with an ultrasonic wave transmitting medium 6. The resin material 5 is, for example, a silicon rubber.

More specifically, the resin member 5 has a partitioning section 51 that divides the space S into a first space S1 and a second space S2 and forms a communication hole 511 through which the spaces S1 and S2 communicate with each other, a first resin section 52 that forms the first space S1 over the first support section 21 in conjunction with the partitioning section 51 and the support film 3, and a second resin section 53 that forms the second space S2 over the second support section in conjunction with the portioning section 51 and the support film 3.

The first resin section 52 comprises a first resin wall section 521 that is provided erectly on an outer periphery of the first support section 21 of the sensor array substrate 2 and a contact section 522 that faces across from the first support section 21 and arranged on one side of the ultrasonic wave receiving/emitting device 10. The contact section 522 is configured to span between the end portion of the first resin wall section 521 that is separated from the support film 3 and the end portion of the partitioning section 51 that is separated from the support film 3. The first resin wall section 521, the contact section 522, and the partitioning section 51 constitute the first resin section mentioned in the claims, and the portion formed by first resin wall section 521, the contact section 522, and the partitioning section 51 is the first recessed section mentioned in the claims. The first resin wall section 521, the contact section 522, and the partitioning section 51 form the first space S1 in conjunction with the support film 3 formed on the sensor array substrate 2, and the first space S1 is sealed from the external space.

The second resin section 53 comprises a second resin wall section 531 that is erectly provided on the support film 3 along the outer periphery of the second support section 22 (which is outside the first support section 21 in a planar direction) and a flexible section 532 that is substantially parallel to the second support section 22 and arranged on the one side of the ultrasonic wave receiving/emitting device 10. The flexible section 532 is configured to span between the end portion of the second resin wall section 531 that is separated from the support film 3 and the end portion of the partitioning section 51 that is separated from the support film 3. The second resin wall section 531, the flexible section 532, and the partitioning section 51 constitute the second resin section mentioned in the claims, and the portion formed by second resin wall section 531, the flexible section 532, and the partitioning section 51 is the second recessed section mentioned in the claims. The first resin wall section 531, the flexible section 532, and the partitioning section 51 form the second space S2 in conjunction with the support film 3 formed on the sensor array substrate 2, and the second space S2 is sealed from the external space.

The partitioning section 51 serves to partition the space S into the first space S1 and the second space S2 as explained previously, and in the sensor plan view the partitioning section 51 is arranged over the support film 3 so as to follow along a border portion between the first support section 21 and the second support section 22. The communication hole 511 formed in the partitioning section 51 is formed between the support film 3 and the partitioning section 51 as shown in FIG. 3, but it is acceptable for the communication hole 511 to be formed through the partitioning section 51. It is also acceptable to provide more than one communication hole 511 that communicates between the first space S1 and the second space S2 or to provide, for example, a single elongated hole 511 whose width extends along a direction of the wall surface of the partitioning section 51 (direction perpendicular to the paper in FIG. 3).

The aforementioned resin material 5 is configured such that the wall thickness dimension T of the first resin wall section 521 and the second resin wall section 531 is, for example, 1 mm and such that the thickness dimension $h_2$ of the contact section 522 and the flexible section 532 is also 1 mm. A height dimension H at which the resin material 5 covers the support film 3 (height dimension H of the first resin wall section 521, the second resin wall section 531, and the partitioning section 51 above the support film 3) is 2 mm. In the sensor plan view, the size of the contact section 522 is 3 mm×3 mm and the size of the flexible section 532 is 3 mm×2 mm. Thus, the surface area of the flexible section 532 is 6 mm². As explained previously, the resin material 5 is silicon rubber. The Young's modulus of silicon rubber becomes approximately $4.0 \times 10^6$ Pa when the temperature of the silicon rubber is changed from room temperature to the body temperature of a person. The flexural rigidity D of the flexible section 532 is $4.44 \times 10-4$ Pa·m³ when calculated according to the aforementioned equation (1) while assuming the Poisson's ratio ν is 0.5.

Although in this embodiment the shape of the flexible section 532 is rectangular in the sensor plan view, in order to facilitate comparing the flexible section 532 to the diaphragms 30, which are circular in the sensor plan view, the flexible section 532 will be assumed to have a circular shape with a radius a of $1.5 \times 10^{-3}$ m based on the fact that the surface area of the flexible section 532 is 6 mm².

Based on the flexural rigidity D, the maximum deflection amount $\omega_{max}$ of the flexible section 532 is $1.78 \times 10^{-10} \times q$ (m) when calculated according to the aforementioned equation (2).

Although in this embodiment the resin material 5 is silicon rubber, the invention is not limited to silicon rubber and any material with similar physical properties is acceptable.

This embodiment is configured such that the volume of the first space S1 is larger than the volume of the second space S2. However, the volumes of the spaces S1 and S2 are not limited to this relationship and it is acceptable to make the volume of the second space S2 larger than the volume of the first space S1 or to make both volumes approximately the same.

Although in this embodiment the second space S2 is formed in one place, it is acceptable to adopt a configuration in which, for example, there are two second spaces S2 arranged on opposite sides of the first space S1 or a configuration in which the second space S2 spans around an entire periphery of the first space S1.

The ultrasonic wave transmitting medium 6 serves to transmit the ultrasonic waves efficiently. Since in this embodiment the device is for inspecting the interior of a human body, any liquid that has approximately the same acoustic impedance as the acoustic impedance of a human body, e.g., water or saline, can be used as the ultrasonic wave transmitting medium 6. It is also acceptable to use a water solution of carboxymethyl cellulose, castor oil, or liquid paraffin as the ultrasonic wave transmitting medium 6.

Figure 4:
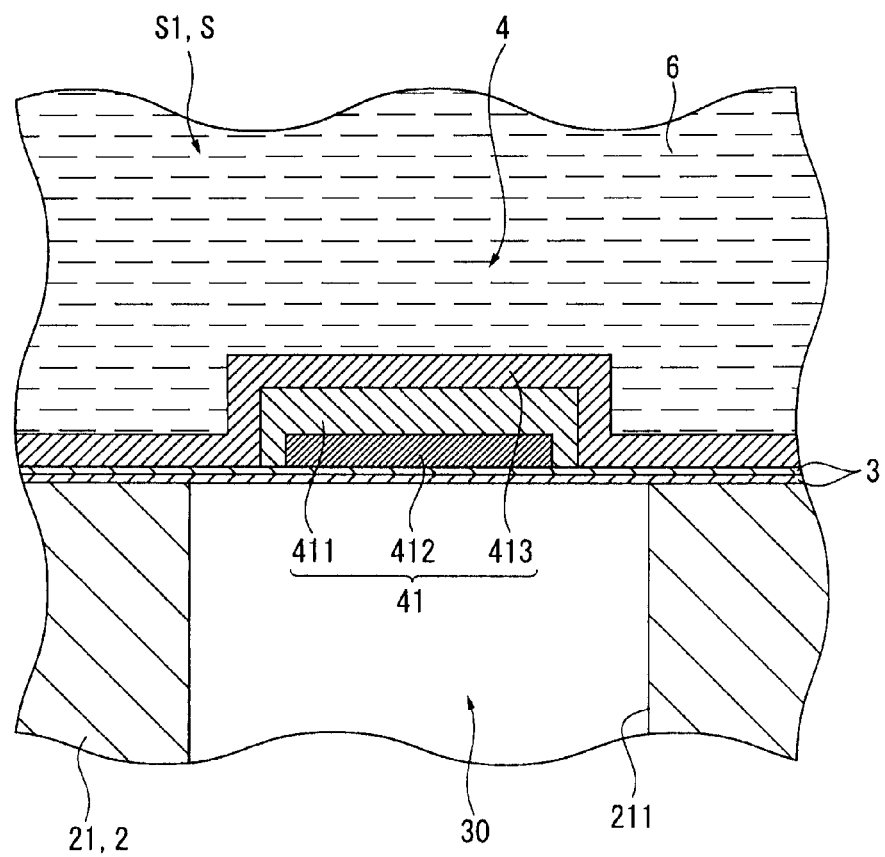
FIG. 4 is a sectional view of an ultrasonic transducer according to the first embodiment.
Figure 5:
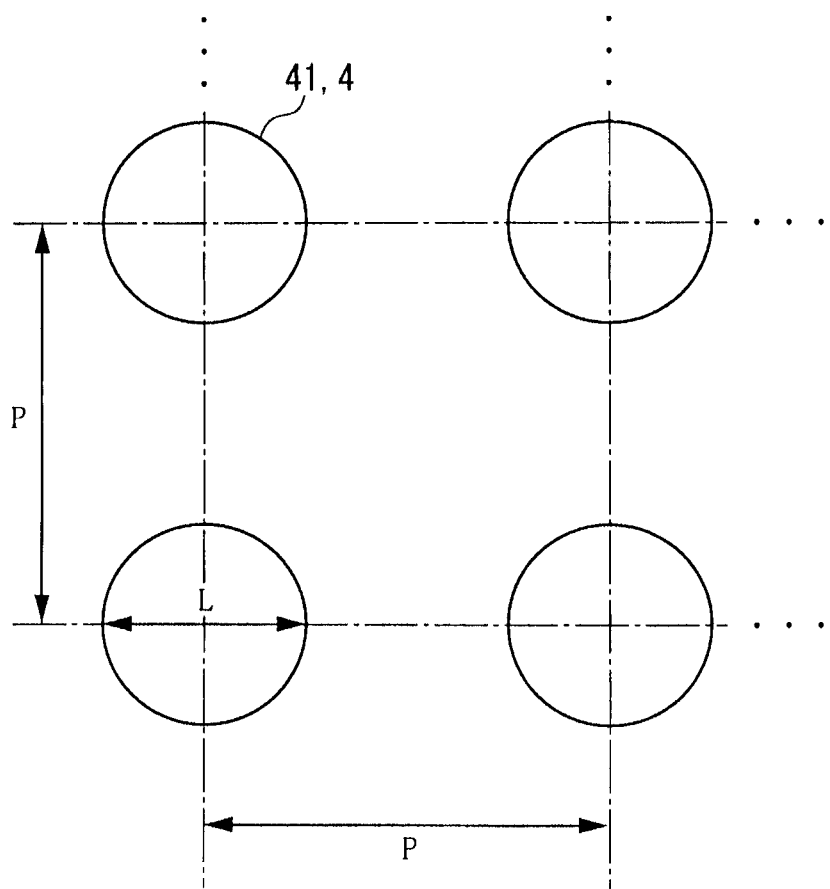
FIG. 5 is a simple sketch illustrating an arrangement layout of an ultrasonic transducers according to the first embodiment.

FIG. 4 is a sectional view of an ultrasonic transducer 4. FIG. 5 is simple diagram showing the arrangement layout of the ultrasonic transducers 4.

The ultrasonic transducers 4 are elements that, for example, emit an ultrasonic wave or receive an ultrasonic wave based on a signal from a control section and send an output to a computational control section. As shown in FIG. 3, the plurality of ultrasonic transducers 4 are provided on the first suppose section 21 of the sensor array substrate 2 and there are, for example, ten columns and ten rows of the ultrasonic transducers 4 as shown in FIG. 3 and the sensor plan view of FIG. 5.

The ultrasonic transducers 4 are made up of the first support section 21 of the sensor array substrate 2, the support film 3, and the piezoelectric bodies 4.

As explained previously, the support section 21 is a portion of the sensor array substrate 2 where the ultrasonic transducers 4 are arranged and an opening section 211 is formed in the position where each of the ultrasonic transducers 4 is arranged.

The support film 3 is formed over the sensor array substrate 2 as explained previously and forms the diaphragms 30 where it blocks the opening sections 211.

Each of the piezoelectric bodies 41 is a film-like member formed on a diaphragm 30 in a center position of the diaphragm 30. Each of the piezoelectric bodies 41 is circular in a plan view and has a diameter dimension L of, for example, 80 µm, which is smaller than the diameter dimension (100 µm) of the opening section 211. The piezoelectric bodies 41 are arranged such that the pitch P of the piezoelectric bodies 41 is 200 µm. Each of the piezoelectric bodies 41 comprises a piezoelectric film 411 and electrodes (a lower electrode 412 and an upper electrode 413) through which a voltage is applied across the piezoelectric film 411.

The piezoelectric film 411 is made of, for example, PZT (lead zirconate titanate) in a film form. In this embodiment, although PZT is used as the material of the piezoelectric film 411, it is acceptable to use any other material that can undergo contraction in a planar direction when a voltage is applied, e.g., lead titanium oxide ($PbTiO_3$), laid zirconium oxide ($PbZrO_3$), lead-lanthanum titanium oxide ($(Pb, La)TiO_3$).

The lower electrode 412 and the upper electrode 413 are electrodes that formed such that they sandwich the piezoelectric film 411 in-between. The upper electrode 413 and the lower electrode 412 are connected to a control section of the test device 1 through leads (not shown) that are formed in the opening section 211.

When a prescribed drive voltage is applied across the electrodes 412 and 413 of the piezoelectric body 41 of the ultrasonic transducer 4, the piezoelectric film 411 elongates and contracts in a planar direction. As a result, the diaphragm 30 vibrates in a film thickness direction and emits an ultrasonic wave toward the contact section 522. The ultrasonic wave emitted from the diaphragm has a frequency corresponding to the frequency of the prescribed drive voltage. That is, the ultrasonic transducer 4 functions as a transmitter that emits ultrasonic waves toward the test object.

The ultrasonic transducer 4 also functions as a receiver that receives ultrasonic waves reflected from the interior of the test object. In the case of reception, the diaphragm 30 is vibrated by a reflected ultrasonic wave and the piezoelectric body 41 produces an electric signal according to the amplitude and frequency of the vibration. The piezoelectric body 41 outputs the electric signal to the control section through the lower electrode 412 and the upper electrode 413.

By switching the mode of the ultrasonic transducer 4 between an ultrasonic wave emitting mode and an ultrasonic wave receiving mode, the control section causes the ultrasonic transducer 4 to function as a receiver or a transmitter.

This embodiment exemplifies a configuration in which the ultrasonic transducers 4 can be used as both transmitters and receivers of ultrasonic waves and one or the other function can be selected by the control section. However, it is acceptable to adopt a configuration in which a plurality of transmitter transducers dedicated to emitting ultrasonic waves and a plurality of receiver transducers dedicated to receiving ultrasonic waves are provided. In such a case, it is acceptable to arrange the transmitter transducers and the receiver transducers alternately (for example) on a single array substrate, or to provide a transmitter array substrate on which a plurality of transmitter transducers are arranged and a receiver array substrate on which a plurality of receiver transducers are arranged and arrange the substrates in different positions.

Operation of Test Device

Figure 6:
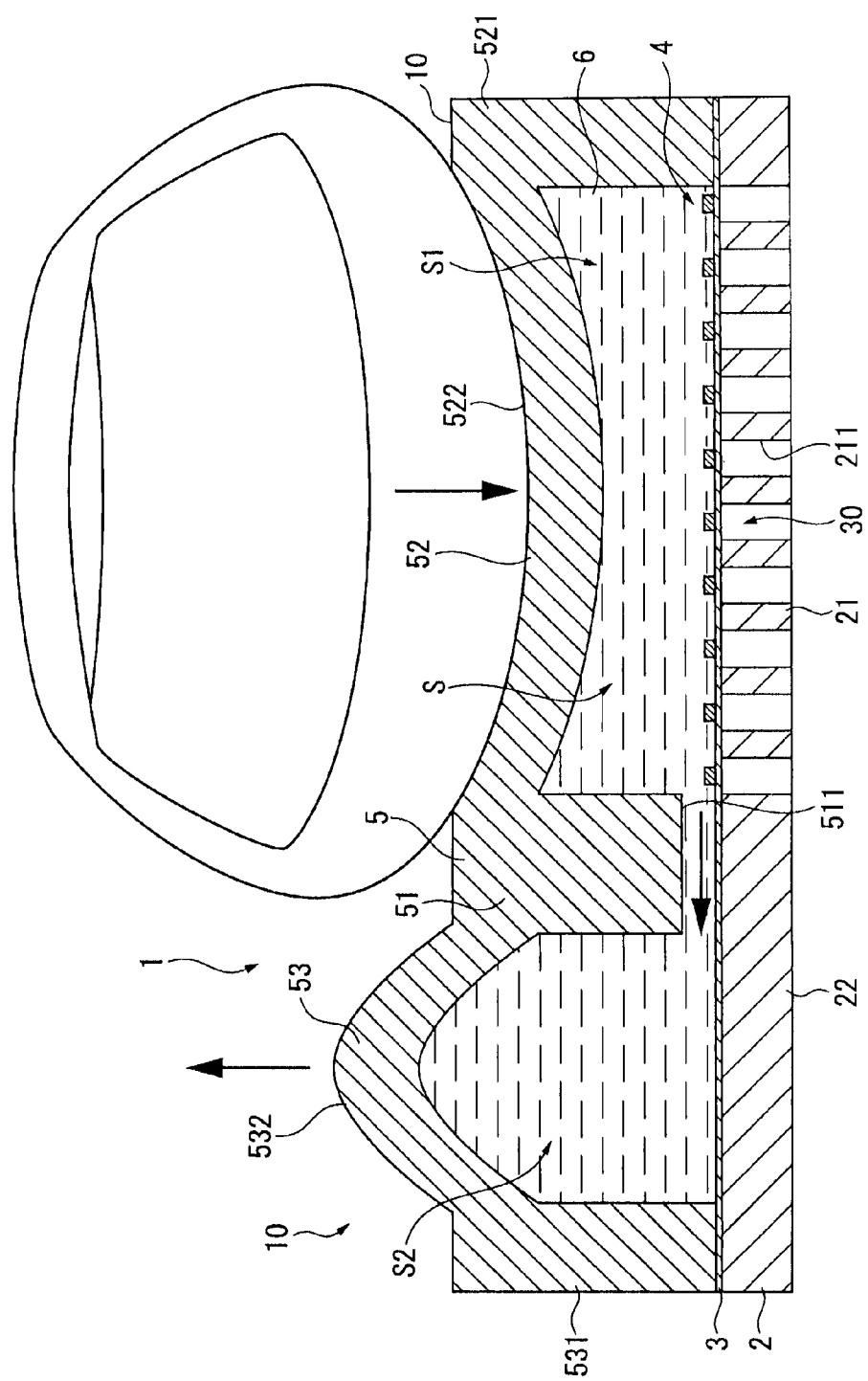
FIG. 6 is a simplified sectional view illustrating the operation of the main parts of an ultrasonic probe according to the first embodiment.

FIG. 6 is a simplified sectional view illustrating the operation of the test device 1.

With the test device 1 explained heretofore, in order to inspect the test object, the ultrasonic probe 100 is manipulated such that the contact section 522 of the test device 1 is put into intimate contact with the test object. When this is done, the deflection amount of the diaphragms 30 changes, but the contact section 522 will typically achieve intimate contact with the test object so long as the maximum deflection amount $\omega_{max}$ of the diaphragms 30 is approximately $1.9 \times 10^{-12} \times q$ (m).

When the ultrasonic probe 100 is pressed against the test object, the contact section 522 deflects toward the support film 3. The deflection causes the volume of the first space S1 to decrease and the internal pressure of the first space S1 to rise.

As explained previously, the flexural rigidity D of the diaphragms 30 is considerably larger than the flexural rigidity D of the flexible section 532. Consequently, as the internal pressure of the first space S1 increases, the ultrasonic wave transmitting medium 6 in the first space S1 flows into the second space S2 and causes the flexible section 532 (which has a smaller flexural rigidity D) to bulge toward the external space. Since the maximum deflection amount $\omega_{max}$ of the diaphragms 30 is approximately $1.9 \times 10^{-12} \times q$ (m) and the maximum deflection amount to of the flexible section 532 is approximately $1.78 \times 10^{-10} \times q$ (m) as explained previously, the flexible section 532 bulges outward and the diaphragms 30 do not exhibit any deflection.

Next, for example, an operator operates input buttons provided on an operating section 200b (see FIG. 1) and thereby transmits an operation signal indicating that a measurement will be started to the control section. The control section then applies a prescribed drive voltage across the electrodes 412 and 413 of the piezoelectric bodies 14. As a result, the ultrasonic transducers 4 emit ultrasonic waves from the diaphragms 30 toward the test object. The ultrasonic waves pass through the ultrasonic wave transmitting body 6 (which has approximately the same acoustic impedance as a human body) and the contact section 522 and into the interior of the test object intimately contacting the contact section 522. Immediately after emission of the ultrasonic waves, the control section stops applying the voltage to the electrodes 412 and 413 of the ultrasonic transducers 4. That is, the control section switches the ultrasonic transducers 4 from the ultrasonic wave emitting mode to the ultrasonic wave receiving mode.

Meanwhile, the ultrasonic waves emitted from the ultrasonic transducers 4 are reflected inside the test object, transmitted back through the contact section 522 and the ultrasonic wave transmitting medium 6, and received by the diaphragm 30. As a result, the diaphragms 30 vibrate in accordance with the intensity of the received ultrasonic waves and the piezoelectric bodies 41 on the diaphragms 30 output detection signals (electric currents) to the control section. Based on the received detection signals, the control section measures an echo image of the interior of the test object and executes a control to display the echo image on the display monitor 200c (see FIG. 1) of the ultrasonic wave observing device 200.

Operational Effects of First Embodiment

Effects exhibited by a detection device 1 according to the first embodiment 1 will now be explained.

In this embodiment, a first space S1 is formed between the first resin section 52 and the region of the support film 3 where the support film 3 blocks the opening sections 211, and the first space 1 is filled with the ultrasonic wave transmitting medium 6. Since the ultrasonic wave transmitting medium 6 is a liquid whose acoustic impedance is substantially equal to the acoustic impedance of a human body, the ultrasonic wave transmitting medium 6 transmits ultrasonic waves readily and without attenuation. Since the contact section 522 is provided in a region facing across from the opening sections 211 of the first resin section 52, when the contact section 522 is put into intimate contact with the test object, ultrasonic waves emitted due to vibration of the diaphragms 30 can transmitted to the inside of the test object and ultrasonic waves reflected inside the test object can be transmitted to the diaphragms 30.

As explained previously, when the contact section 522 of the first resin section 52 contacts the test object, the contact section 522 deflects and the internal pressure of the first space S1 increases. Meanwhile, in this embodiment, the second resin section 53 forms the second space S2, which communicates with the first space S1, the flexible section 532 is provided on the second resin section 53, and the flexible section 532 has a smaller flexural rigidity D than the flexural rigidity D of the diaphragms 30. Consequently, even when the internal pressure inside the first space S1 is high, the flexible section 532 bulges toward the external space and the ultrasonic wave transmitting medium 6 inside the first space S1 flows into the second space S2.

Thus, deformation of the diaphragm 30 can be suppressed even if the test object is in intimate contact with the contact section 522 and the internal pressure of the first space S1 increases. Consequently, when a voltage is applied to the piezoelectric bodies 41 and the diaphragm 30 are made to vibrate or when an ultrasonic wave is received by the diaphragms 30 such that the diaphragms 30 vibrate, the vibration of the diaphragms 30 is not attenuated and the ultrasonic waves can be emitted and received in a favorable manner.

Second Embodiment

A test device 1A according to a second embodiment will now be explained based on the drawings.

Figure 7:
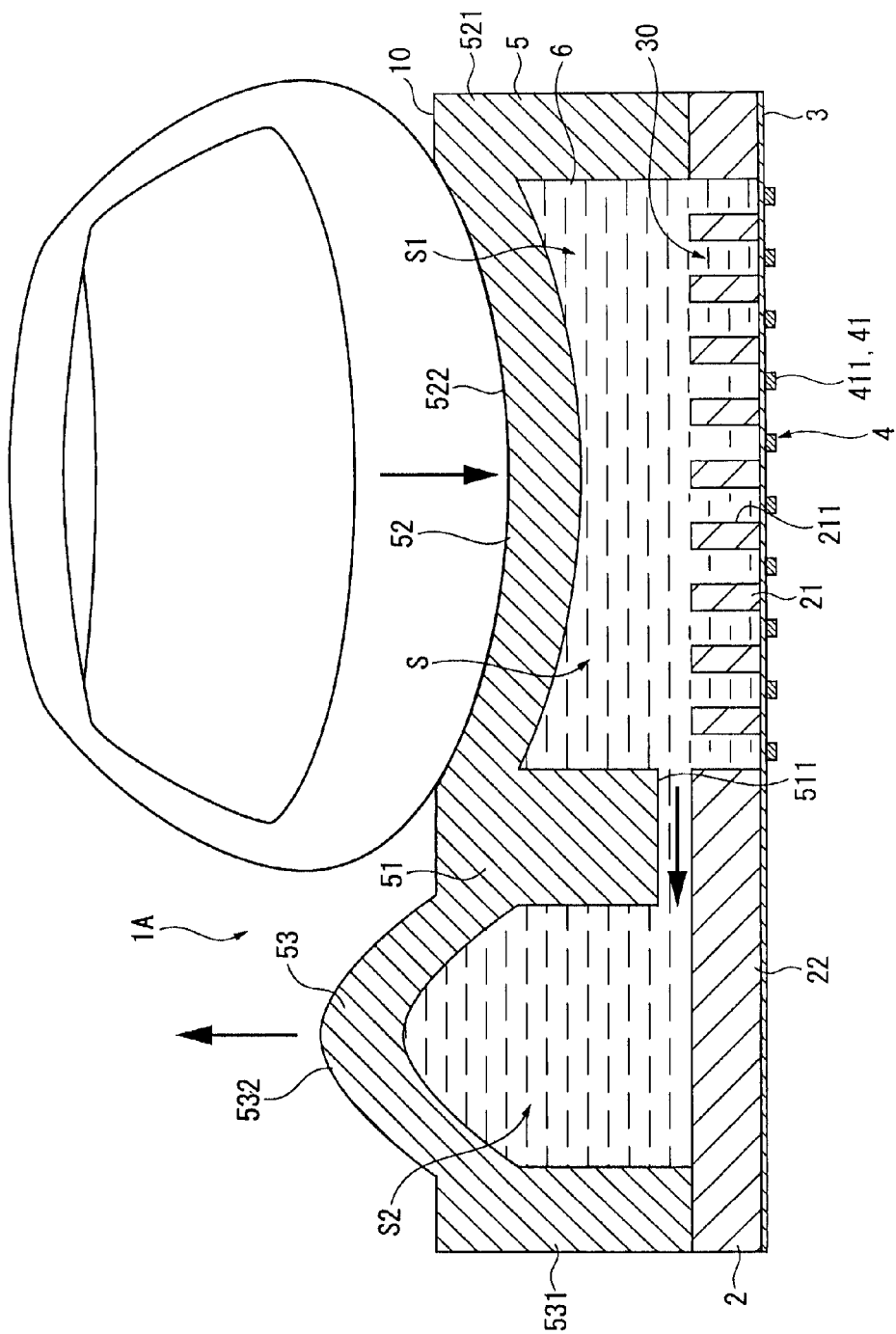
FIG. 7 is a simplified sectional view illustrating the operation of the main parts of an ultrasonic probe according to a second embodiment of the present invention.

FIG. 7 is a simplified sectional view illustrating the operation of the test device 1A according to the second embodiment. In this explanation, parts that are the same as the parts of the previously explained embodiment are assigned the same reference numerals and explanations thereof are omitted. The same applies to all embodiments explained hereinafter.

The test device 1A according to the second embodiment differs from the first embodiment in that a space S is formed between the sensor array substrate 2 and the resin material 5 and the support film 3 is arranged on the side of the sensor array substrate 2 that faces toward external space. In short, the ultrasonic transducers 4 are arranged in different positions than in the first embodiment.

The test device 1A adopts a configuration in which the support film 3 is arranged on the side of the sensor array substrate 2 that faces toward the external space and the piezoelectric bodies 41 are arranged on the opposite side of the support film 3 as the side that faces toward the contact section 522 of the first resin section 52. That is, the piezoelectric bodies 41 are arranged outside the first space S1. With this configuration, the interiors of the opening sections 211 of the first support section 21 are part of the first space S1 and the interiors of the opening sections 211 are filled with the ultrasonic wave transmitting medium 6.

While the ultrasonic transducers 4 of the first embodiment are configured to emit ultrasonic waves from the sides of the piezoelectric films 411 that face away from the support film 3, in this embodiment the ultrasonic transducers 4 are configured to emit ultrasonic waves from the sides of the piezoelectric films 411 that face toward the support film 3.

With the test device 1A according to the second embodiment, the same effects can be obtained as with the first embodiment even if the ultrasonic transducers 4 are configured such that the ultrasonic waves are emitted from the sides of the piezoelectric films 411 that face the support film 3. With this configuration, even if the contact section 522 is pressed strongly against the test object such that the contact section 522 deflects greatly toward the support film 3, the contact section 522 will contact the support section 21 of the sensor array substrate 2 and will not contact the piezoelectric bodies 41 or the support film 3. Consequently, the piezoelectric bodies 41 and the support film 3 can be prevented from being damaged.

Variation of the Second Embodiment

Figure 8:
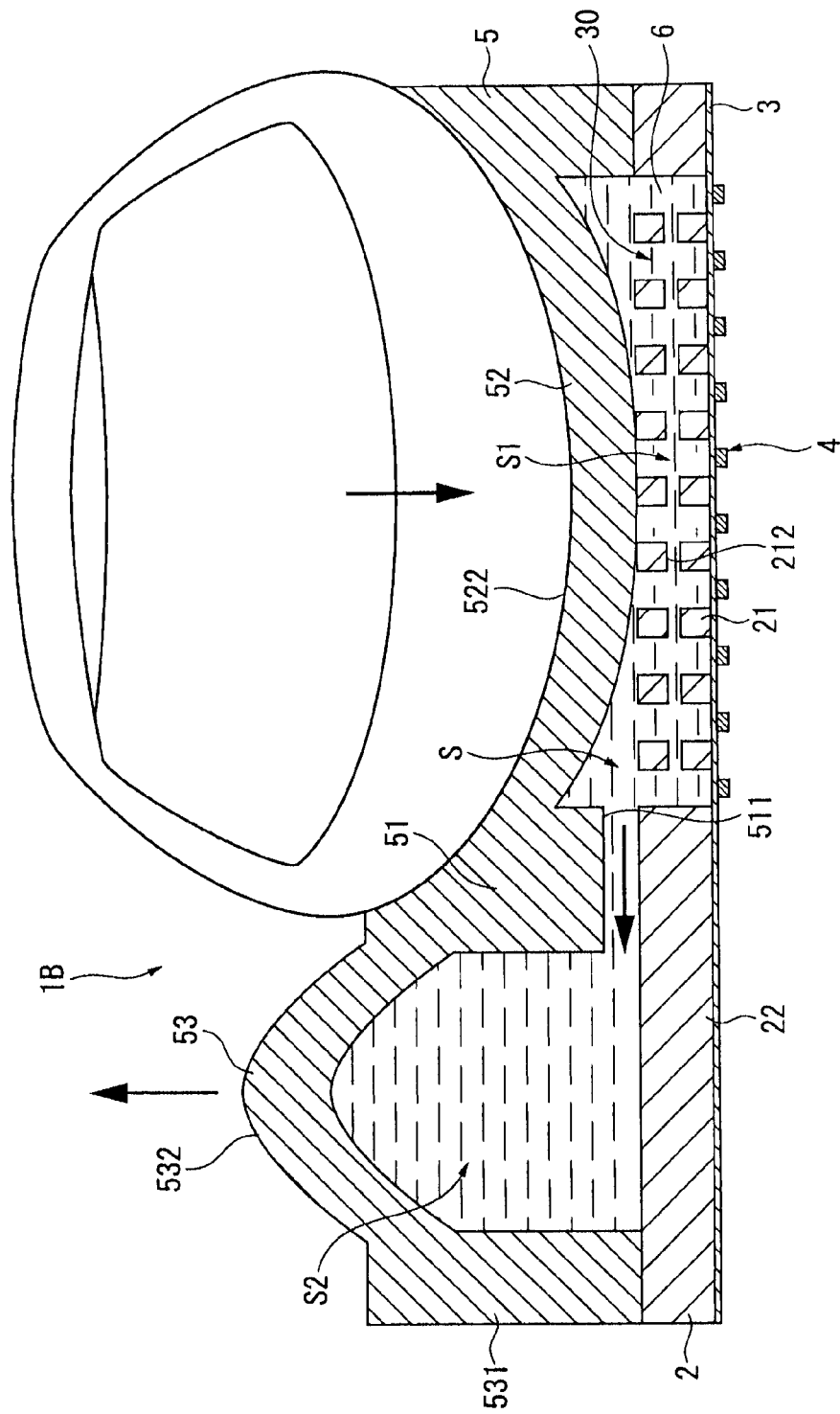
FIG. 8 is a simplified sectional view illustrating the operation of the main parts of an ultrasonic probe according to a variation of the second embodiment.

FIG. 8 is a simplified sectional view illustrating the operation of a test device 1B according to a variation of the second embodiment.

In this variation, a through hole 212 that extends in a direction perpendicular to the film thickness direction of the support film 3 is formed in the first support section 21.

When the interior of the test object presses strongly against the contact section 522, the contact section 522 contacts the first support section 21 as shown in FIG. 8. With the configuration of the second embodiment shown in FIG. 7, if the contact section 522 contacts the first support section 21, then the first space S1 will be divided by the first resin section 52 and the ultrasonic wave transmitting medium 6 located on the side of the first space S1 that is closer to the second space S2 will flow readily to the second space S2. However, there will be a possibility that the ultrasonic wave transmitting medium 6 located on the side of the first space S1 farther from the second space S2 will not flow readily to the second space S2 due to the first support section 21. Additionally, since the contact section 522 contacts the first support section 21, there is a possibility that the opening sections 211 will blocked by the contact section 522 and the diaphragms 30 will be deflected by the increased internal pressure of the first space S1.

With the configuration of the variation shown in FIG. 8, even if the contact section 522 contacts the support section 21, the ultrasonic wave transmitting medium 6 located on the side of the first space S1 that is farther from the second space S2 can flow toward the second space S2 through the through hole 212 formed in the first support section 21. In this way, the same effects as the embodiments can be obtained.

Additionally, with this variation it is possible to prevent the diaphragms 30 from being deflected by an increase of the internal pressure of the first space S1 when the contact section 522 contacts the first support section 21 and the opening sections 211 become blocked by the contact section 522.

Third Embodiment

A test device 1C according to a third embodiment will now be explained based on the drawings. FIGS. 3 and 4 will be referred to as appropriate in the explanation.

Figure 9:
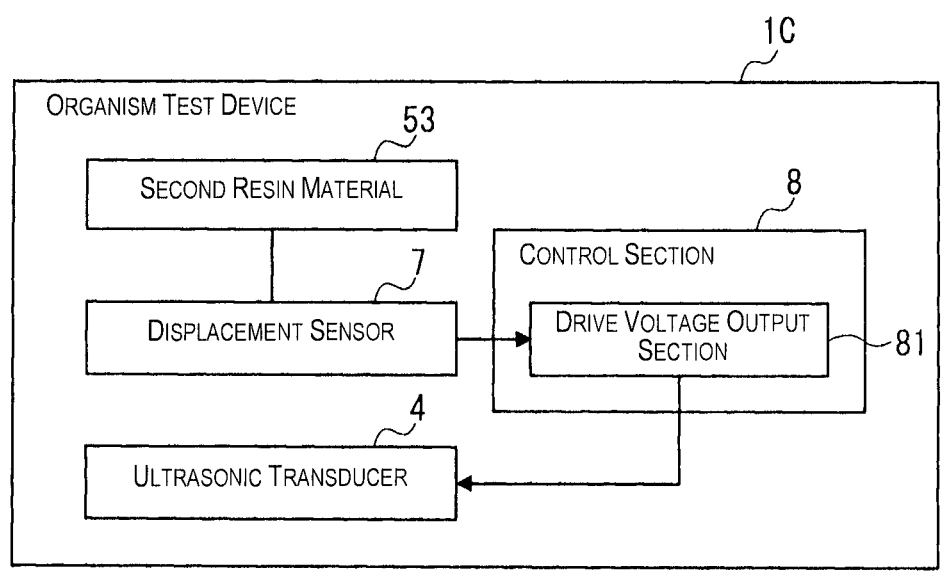
FIG. 9 is a block diagram of an ultrasonic probe according to a third embodiment of the present invention.

FIG. 9 is a block diagram of the test device 1C according to the third embodiment.

The test device 1C according to the third embodiment differs from the previously explained embodiments in that it is provided with a displacement sensor 7 (corresponding to the displacement detecting section) that detects a displacement of the second resin section 52 and a control section 8 that controls the test device 1C in accordance with a detection signal from the displacement sensor 7.

The displacement sensor 7 detects displacement of the flexible section 532 of the second resin section 53. The displacement sensor 7 outputs a detection signal to the control section 8 when it detects a displacement of the flexible section 532. The displacement sensor 7 is a contact sensor and can be exemplified with a differential transformer. A differential transformer detects displacement based on a voltage difference occurring in two coils due to electromagnetic induction. However, the invention is not limited to a contact type sensor and it is acceptable to use a non-contact type sensor. For example, it is acceptable to use an electrostatic capacitance type sensor that detects a displacement based on a change of electrostatic capacitance, an ultrasonic sensor that detects a displacement based on a reflection time of an ultrasonic wave, or a strain detecting element that is arranged on the flexible section 532 and detects a displacement.

The control section 8 has a drive voltage generating section 81 (corresponding to the ultrasonic wave generating section) that executes a process of outputting a voltage signal to the electrodes 412 and 413 of the ultrasonic transducers 4, receiving voltage signals outputted from the piezoelectric bodies 41, and measuring a pulse, a blood pressure, or another blood flow state based on the received voltage signals.

The drive voltage output section 81 outputs a voltage signal to the electrodes 412 and 413 of the ultrasonic transducers 4 when it receives a detection signal from the displacement sensor 7. Meanwhile, when it does not receive a detection signal from the displacement sensor 7, the drive voltage output section 81 determines that the test object is separated from the contact section 522 and stops outputting the voltage signal to the electrodes 412 and the 413.

The drive voltage output section 81 also detects voltage signals outputted from the piezoelectric bodies 41 when the piezoelectric bodies 41 receive ultrasonic waves and executes a process of measuring a pulse, a blood pressure, or another blood flow state based on the voltage signals.

When the contact section 522 is touched against the test object, the contact section 522 deflects inward and the ultrasonic wave transmitting medium 6 flows through the communication hole 511 and into the second space S2.

Consequently, the flexible section 532 surrounding the second space S2 bulges outward and the displacement sensor 7 detects the resulting displacement and sends a detection signal to the drive voltage output section 81 of the control section 8.

When the drive voltage output section 81 receives the detection signal from the displacement sensor 7 and thereby detects that the contact section 522 has contacted the test object, the drive voltage section 81 changes the ultrasonic transducers 4 to the ultrasonic wave emitting mode and outputs a voltage signal to the electrodes 412 and 413 of the ultrasonic transducers 4. As a result, as explained previously, the electrodes 412 and 413 apply a prescribed voltage to the piezoelectric films 411 based on the voltage signal and ultrasonic waves are emitted from the diaphragms 30 to the contact section 522. The drive voltage output section 81 then changes the ultrasonic transducers 4 to the ultrasonic wave receiving mode.

When the diaphragms 30 receive the ultrasonic wave reflected from the test object contacting the contact section 522, the diaphragms 30 output voltage signals to the drive voltage output section 81 of the control section 8 and the drive voltage output sections 81 executes a process of capturing an echo image of the interior of the test object based on the voltage signals.

Effects that the test device 1C according to the third embodiment exhibit in addition to the effects of the first embodiment will now be explained.

With this embodiment, the control section 8 can detect if the contact section 522 has contacted the test object and the drive voltage output section 81 of the control section 8 outputs a voltage signal to the electrodes 412 and 413. As a result, the ultrasonic waves can be emitted reliably and the ultrasonic waves can reliably reach the test object only when the test object is contacting the contact section 522.

Variations of the Embodiments

The present invention is not limited to the previously explained embodiments, and various changes and improvements can be made without departing from the scope of the invention as defined by the claims.

In the previously explained embodiments, the space S is divided into a first space S1 and a second space S2 by a partitioning section 51, but it is acceptable not to provide a partitioning section 51. In such a case, the device is configured such that when the contact section 522 touches against a test object and the contact section 522 deflects inward, the ultrasonic wave transmitting medium 6 can flow inside the space S and cause the flexible section 532 to bulge outward.

Although in the previously explained embodiments the first resin section 52 and the second resin section 53 are made of the same material and have the same thickness dimension $h_2$ and T, it is acceptable for these sections to be made of different materials and configure to have different thickness dimensions. It is also acceptable to make only the flexible section 532 of a different material and with a different thickness dimension. It is also acceptable to make the flexible section 532 have a circular shape in the sensor plan view.

Although in the previously explained embodiments the flexible section 532 is arranged to face across from the second support section 22, it is acceptable for the flexible section 532 to be formed on a side of the second resin section 53.

Although in the previously explained embodiments the size of the contact section 522 of the first resin section 52 is 3 mm×3 mm in the sensor plan view, the size of the contact section 522 is not limited to this and it is acceptable to configure the contact section 522 in accordance with the size and shape of the test object that it will be contacting.

Although in the previously explained embodiments a communication hole 511 is provided to communicate between the first space S1 and the second space S2, it is acceptable to provide tube or other pipe-like member to communicate between the first space S1 and the second space S2. When a pipe-like member is used, it is acceptable for the second space to be formed solely by a bag-like second resin section 53 and for the second resin section 53 not to be fixed to the support film 3 and the sensor array substrate 2.

In the embodiments shown in FIG. 3, FIG. 6, and FIG. 8, the second space S2 is explained as being arranged over the second support section 22 of the sensor array substrate 2 for convenience. However, the invention is not limited to this arrangement and it is acceptable to arrange the second space S2 in a position that is not over the sensor array substrate 2.

In the example shown in FIG. 2A, the flexible section 532 is exposed on a portion of the case 100a. With this arrangement, since the amount of displacement of the flexible section 532 can be checked visually, it is easy to determine if the contact section 522 is in intimate contact with the test object.

Meanwhile, in the variation shown in FIG. 2B, the flexible section 532 is not exposed on the outside of the case 100a. Consequently, there is no risk of accidentally pressing the flexible section 532 while using the device and disrupting the intimate contact between the contact section 522 and the test object. That is, each of the variations shown in FIG. 2A and FIG. 2B has unique advantages.

Although in the previously explained embodiments the support film 3 is provided over an entire surface of the sensor array substrate 2, it is acceptable to provide the support film 3 only on the portions of the first support section 21 where the support film 3 will block the opening sections 211.

Although in the previously explained embodiments the opening sections 211 are configured to pass through the sensor array substrate 2, the invention is not limited to such a configuration and it is acceptable for the opening sections to be configured as recesses. In such a case, the support film 3 is formed such that it blocks the openings of the recesses. It is also acceptable for the support film 3 to be formed on a bottom surface of the recesses.

General Interpretation of Terms

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "element" when used in the singular can have the dual meaning of a single part or a plurality of parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

While only selected embodiments have been chosen to illustrate the present invention, it will be apparent to those skilled in the art from this disclosure that various changes and modifications can be made herein without departing from the scope of the invention as defined in the appended claims. Furthermore, the foregoing descriptions of the embodiments according to the present invention are provided for illustration only, and not for the purpose of limiting the invention as defined by the appended claims and their equivalents.

What is claimed is:

1. An ultrasonic probe comprising:
   an ultrasonic transducer;
   a liquid filled section filled with a liquid;
   a contact section including a deformable resin material, being positioned outside the ultrasonic transducer, and forming a portion of the liquid filled section; and
   a flexible section including the deformable resin material and forming a portion of the liquid filled section,
   the ultrasonic transducer being configured to transmit ultrasonic waves through the contact section,
   the flexible section being configured to bulge into an interior space of a case of the ultrasonic probe.

2. An ultrasonic image diagnostic device equipped with the ultrasonic probe according to claim 1.

* * * * *